United States Patent [19]

Mendoza et al.

[11] 4,235,840
[45] Nov. 25, 1980

[54] SAMPLE TRANSFER ARM ASSEMBLY

[75] Inventors: Daniel F. Mendoza; Charles E. Hodgson, both of Silver Spring, Md.

[73] Assignee: Baxter Travenol Laboratories, Inc., Deerfield, Ill.

[21] Appl. No.: 37,679

[22] Filed: May 10, 1979

[51] Int. Cl.³ .............................................. G01N 1/14
[52] U.S. Cl. .................................... 422/64; 73/425.6; 422/100
[58] Field of Search ..................... 422/64, 63, 72, 100; 73/425.6, 425.4 P, 425.4 R; 141/130

[56] References Cited

U.S. PATENT DOCUMENTS

| | | | |
|---|---|---|---|
| 3,081,158 | 3/1963 | Winter | 422/64 |
| 3,178,266 | 4/1965 | Anthon | 422/64 |
| 3,252,330 | 5/1966 | Kling | 422/64 |
| 3,266,322 | 8/1966 | Negersmith et al. | 422/64 |
| 3,449,959 | 6/1969 | Grimshaw | 422/64 |
| 3,801,283 | 4/1974 | Shapiro et al. | 73/425.4 P |

Primary Examiner—R. E. Serwin
Attorney, Agent, or Firm—Henry W. Collins; Paul C. Flattery; Thomas R. Vigil

[57] ABSTRACT

The assembly includes a horizontally disposed sample transfer arm which is mounted to and extends radially outwardly from a vertically positioned cylindrical support member. A drive shaft is coupled by a drive mechanism to the cylindrical member for rotating the cylindrical member a predetermined arcuate distance to move the transfer arm between a first position over a first receptacle and a second position over a second receptacle. Locating stops associated with the cylindrical support member define and limit the arcuate movement of the arm. The drive mechanism includes a lost motion clutch assembly including a flat cam member which has a generally rectangular cross-section, which is fixed to the top of the drive shaft and which is received in a slot in the cylindrical member that extends axially inwardly from one end of the cylindrical member and that has a generally rectangular cross-section greater than the rectangular cross section of the cam member. A wide, generally U-shaped spring clip has a flat bight portion situated within the slot at the inner end thereof and has two leg portions which extend toward each other and which have opposed outer ends which are spaced apart a distance less than the thickness of the cam member. The cam member is received between and engaged by the leg portions of the spring clip within the slot in the cylindrical support member. Over-rotation of the drive shaft in excess of the predetermined arcuate distance will cause the cam to turn within the slot and spread the opposed leg portions of the spring clip as movement of the arm is blocked by engagement of the arm with one of the locating stops at one end of the arcuate path of travel of the arm thereby to prevent damage to the assembly.

9 Claims, 9 Drawing Figures

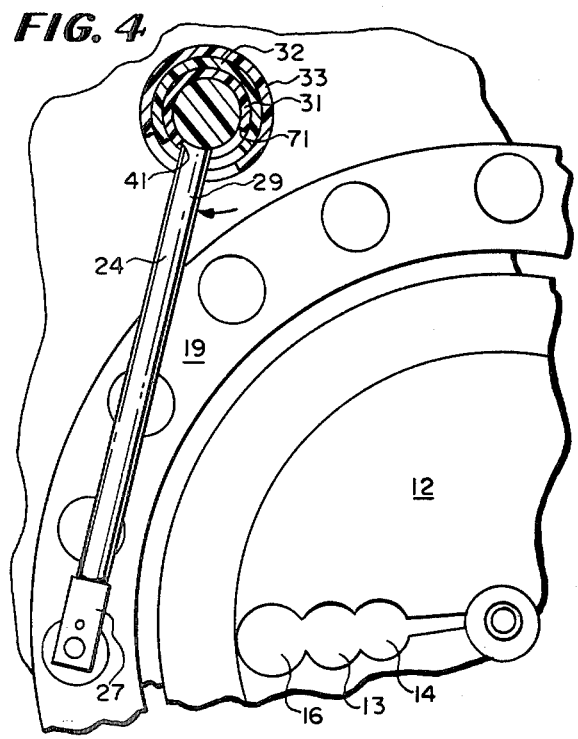
FIG. 4
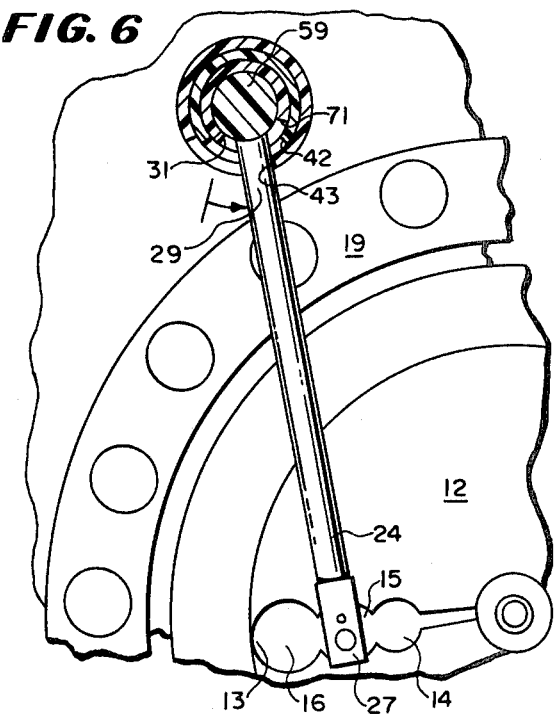
FIG. 6
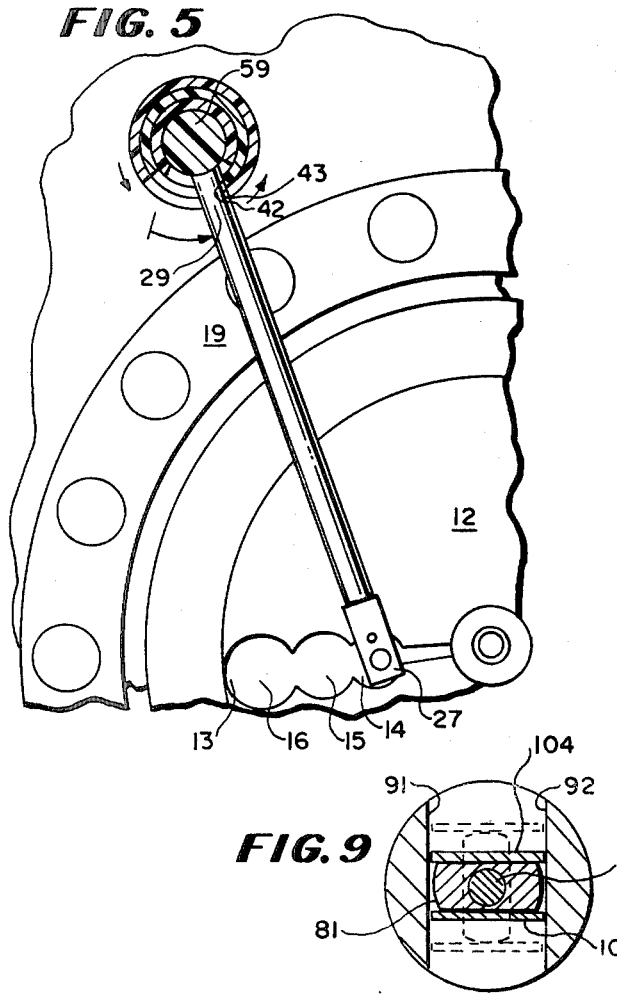
FIG. 5
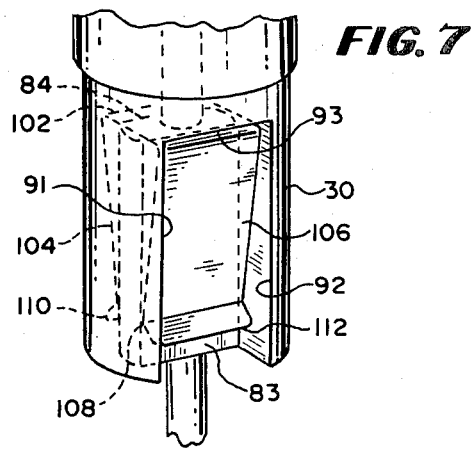
FIG. 7
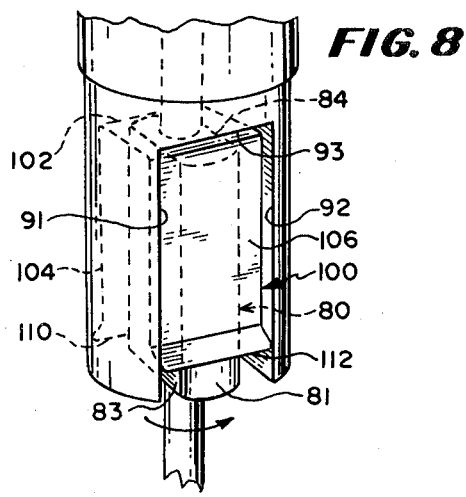
FIG. 8
FIG. 9

SAMPLE TRANSFER ARM ASSEMBLY

BACKGROUND OF THE INVENTION

1. Field of the Invention

The present invention relates to an improved sample transfer arm assembly and more specifically to a lost motion clutch mechanism incorporated within the assembly for permitting overrotation of the drive shaft without damage to the assembly when arcuate movement of an arm of the assembly is limited by engagement with a locating stop.

2. Description of the Prior Art

In one type of centrifugal automatic chemical analysis apparatus, a transfer disc having a plurality of spoke like channels formed therein with each channel having at least three wells is utilized in mixing sample and reagent and transferring the mixture to a reaction chamber. Starting from the inner radial end of each channel, there are first and second wells each of which forms either a reagent receiving well or a sample receiving well. The outermost well forms a mixing well. Such transfer disc with, for example, 36 channels, has each of the first and second wells filled with sample and reagent with one channel being filled with water. Then the transfer disc is inserted in a centrifugal chemical analysis apparatus such as the Rotochem$_{TM}$ sold by American Instrument Company, a division of Baxter Travenol Laboratories, Inc. of Deerfield, Ill. The apparatus is then operated to rotate the transfer disc to cause sample to mix with reagent and then to be ejected from the mixing well by centrifugal force through an outer opening at the end of each channel in the transfer disc and into a reaction chamber or cuvette in an annular ring positioned around and rotatable with the transfer disc.

Light transmitting windows are provided at the top and bottom of each reaction cuvette and the annular ring is positioned to rotate past a light beam located on one side of the annular ring. A photosensitive device located on the other side of the annular ring in the light path of the light beamed from the light source senses the amount of light transmitted to monitor thereby the reaction and, upon each rotation of a reaction chamber 360°, the rate of the reaction taking place in each reaction chamber.

In preparing a plurality of samples for analysis in the centrifugal chemical analysis apparatus, the transfer disc is placed on an automatic reagent and sample filling device such as the Rotofill$_{TM}$ sold by American Instrument Company, a division of Travenol Laboratories, Inc., of Deerfield, Ill. The automatic sample and reagent filling device is provided with a turntable on which the transfer disc is positioned and an annular sample tray supporting a plurality of sample cuvettes in a ring is positioned around the transfer disc and on the turntable. Positioned above the turntable is a stationary reagent arm for dispensing reagent to one or the other of the first and second wells in each channel of the transfer disc.

Additionally, a sample transfer arm is positioned over the turntable and is mounted to and extends radially outwardly from a cylindrical support mounted on a rotatable and reciprocal drive shaft so that the transfer arm can be rotated about one end thereof a predetermined arcuate extent. To insure proper positioning of the transfer arm at a first position over a sample containing cuvette in the same tray, a cylindrical sleeve with a generally rectangularly shaped window through which the arm extends is received over the cylindrical support with one side edge of the window forming a stop which is located and fixed in place to locate the outer end of the transfer arm, when it engages that side edge of the window, over a sample cuvette in the sample tray. Then, a second cylindrical sleeve having a similar generally rectangularly shaped window is positioned over the first sleeve with the window thereof in registry with the first window and with an edge thereof forming a stop to locate the outer end of the transfer arm at the other end of its arcuate path of travel over the innermost well of the transfer disc. Lastly, a third cylindrical sleeve is received over the first two sleeves and has a generally rectangularly shaped window which is in registry with the first two windows. The third sleeve is rotatable between one releasably fixed locating position where an edge of the window therein is radially in line with the locating edge of the window in the second sleeve and a second releasably fixed locating position where the stop forming edge of the window is now positioned to stop movement of the transfer arm with the outer end thereof positioned over the second well of a channel in the transfer disc.

In operation of the automatic reagent and sample filling device, water is placed in the wells of one channel. Then the turntable is indexed a predetermined amount to rotate a first sample cuvette in the sample tray to a position under the outer end of the sample transfer arm. Then the drive shaft, cylindrical support and transfer arm are moved downwardly to bring an aspirating dip tube mounted on the outer end of the transfer arm into the sample cuvette for aspirating a predetermined amount of sample into the dip tube. Then the drive shaft, cylindrical support and transfer arm are moved upwardly and rotated counterclockwise to move the sample arm against the side edge of the window in the second sleeve to locate the outer end of the sample transfer arm over the innermost well, unless, of course, the third sleeve had been moved to locate the edge of the window thereof to stop movement of the transfer arm with the outer end thereof over the second well. In either event, the drive shaft, cylindrical support and transfer arm are lowered to lower the dip tube into the well and the predetermined amount of sample in the dip tube is ejected into the well. Then the sample transfer arm is raised and rotated clockwise to bring the transfer arm back to its first position and the turntable is indexed to position the next sample cuvette under the dip tube at the end of the sample transfer arm to repeat the above sequence of operations. Reagent, of course, is dispensed into the first or second well by dip tubes extending from the reagent arm each time a new channel is positioned under the reagent arm.

In the operation of the automatic reagent and sample filling device, exact control of the rotational movement of the drive shaft is not readily obtainable. As a result, stress and a bending moment are placed on the transfer arm when it engages one of the stop forming side edges of one of the windows when the drive shaft rotates more than the predetermined arcuate extent. Also a torque is placed on the drive shaft and the cylindrical support for the transfer arm. These stresses, bending moments and torque forces have resulted in damage to the device and failure of the device to operate properly.

As will be described in greater detail hereinafter, the present invention provides a solution to this problem of bending moments and torque forces being placed on the sample transfer arm assembly by providing a lost motion clutch assembly in a drive arrangement between the cylindrical support and the drive shaft.

The lost motion clutch assembly permits overrotation of the drive shaft beyond the predetermined arcuate extent without damage to the transfer arm assembly when arcuate movement of the transfer arm is limited by engagement thereof with one of the locating stops defined by a side edge of one of the windows in one of the sleeves.

SUMMARY OF THE INVENTION

According to the present invention there is provided an improved sample transfer arm assembly for use in a device for transferring liquid sample from a first receptacle to a second receptacle, said assembly including a sample transfer arm, support means for supporting said sample transfer arm with said arm extending normal to and from the axis of said support means, locating means for locating and limiting arcuate movement of said arm about said axis of said support means, drive means including a drive shaft for rotating said arm support means a predetermined arcuate extent between a first position where the outer end of said arm is located over the first receptacle and at least one other position where said outer end of said transfer arm is located over the second receptacle, and with drive means including lost motion clutch means between said drive shaft and said arm support means for permitting overrotation of said drive shaft beyond said predetermined arcuate extent without damage to said sample transfer arm when arcuate movement of said sample transfer arm is limited by engagement thereof with said locating means.

BRIEF DESCRIPTION OF THE DRAWINGS

FIG. 4 is a fragmentary sectional view taken along line 4—4 of FIG. 2, shows the outer end of the sample transfer arm located over a sample cuvette and shows the positions of locating stops for locating and limiting arcuate movement of the transfer arm when the outer end thereof is over a sample cuvette.

FIG. 5 is a fragmentary sectional view similar to FIG. 4 showing the locating stops when the outer end of the sample transfer arm is positioned over the innermost well in a channel in a transfer disc.

FIG. 6 is a fragmentary sectional view similar to FIGS. 4 and 5 showing the position of the locating stops when the outer end of the transfer arm is positioned over the second well in the channel of the transfer disc.

FIG. 7 is a fragmentary vertical perspective view showing the cylindrical support member for the transfer arm and a lost motion clutch assembly in a drive arrangement between the lower end of the cylindrical support member and a drive shaft of the sample transfer arm assembly.

FIG. 8 is a fragmentary vertical perspective view similar to FIG. 7 showing the position of the clutch assembly with a cam of the clutch assembly rotated within a spring clip of the clutch assembly so as to spread apart the leg portions of the spring clip to take up lost motion when the drive shaft is rotated an arcuate extent greater than a predetermined arcuate extent and the transfer arm is bearing against one of the locating stops.

FIG. 9 is a transverse section of the clutch assembly of FIG. 7 showing, in phantom lines, the cam element positioning of FIG. 8.

DESCRIPTION OF THE PREFERRED EMBODIMENT

Figure 1:
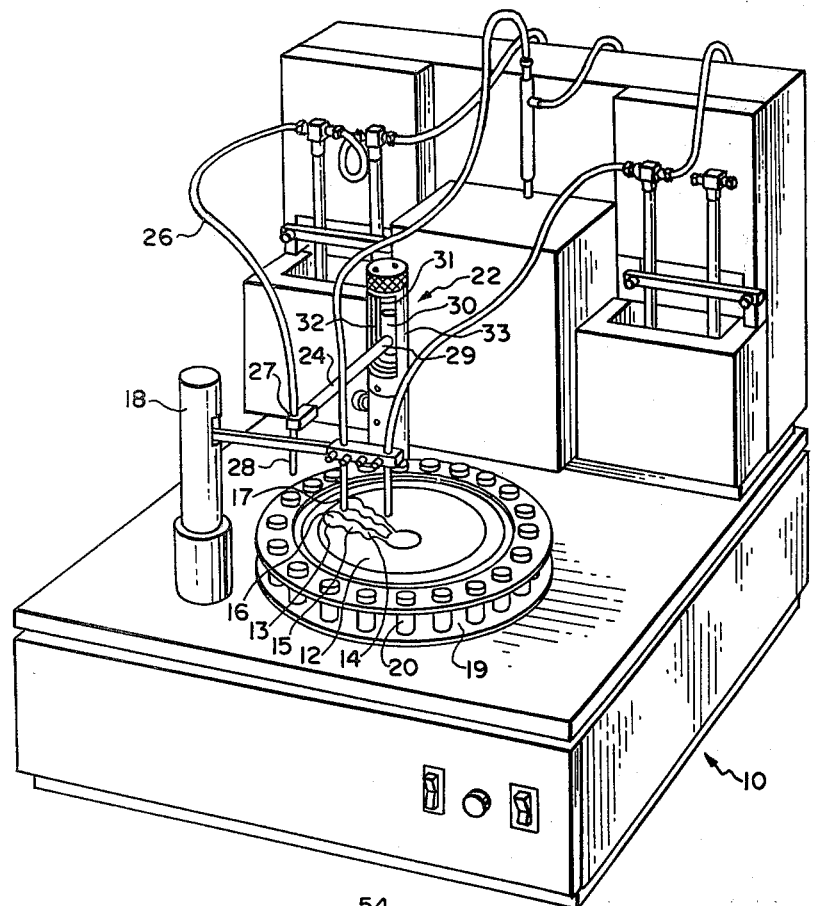
FIG. 1 is a perspective view of an automatic sample and reagent filling device.

Referring now to FIG. 1 in greater detail, there is illustrated therein an automatic sample and reagent filling device 10 of the type sold by American Instrument Company of Silver Spring, Maryland, a division of Travenol Laboratories, Inc., of Deerfield, Ill. under the trademark "ROTOFILL". The device 10 is particularly adapted for filling a transfer disc 12 which has thirty six channels 13 each of which has a first or inner well 14, a second well 15 and a third or outer well 16 with reagent and sample. Reagent is placed in the well 14 or the well 15 by a dip tube 17 located above the transfer disc 12 and depending from a reagent arm assembly 18. Positioned around the transfer disc 12 is an annular sample tray 19 containing a plurality, i.e., thirty six, of sample cuvettes 20. Although hidden from view it is to be understood that the transfer disc 12 and the annular sample tray 19 are supported on a turntable of the device 10.

Figure 2:
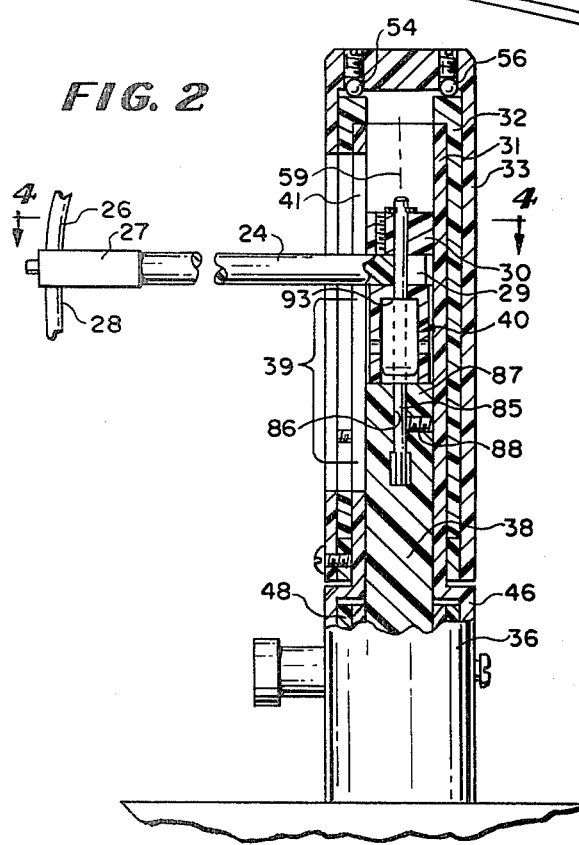
FIG. 2 is a vertical view with portions broken away of the sample transfer arm assembly of the filling device shown in FIG. 1.
Figure 3:
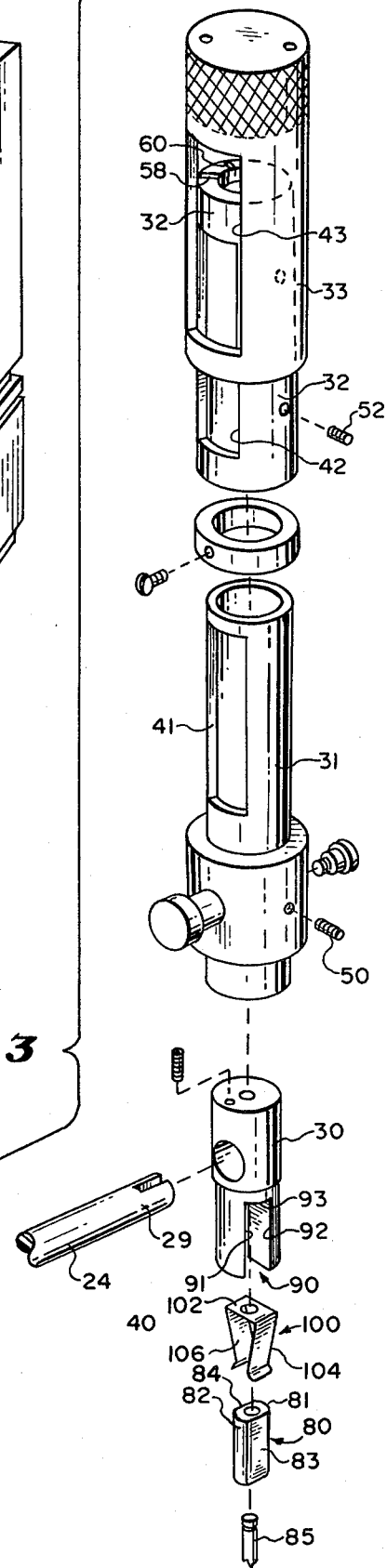
FIG. 3 is an exploded perspective view of the sample transfer arm assembly.

The automatic reagent and sample filling device 10 also includes a sample transfer arm assembly 22. The sample transfer arm assembly 22 includes a sample transfer arm 24 which has a tubing 26 supported at the outer end 27 thereof with a dip tube portion 28 of the tubing 26 depending from the outer end 27 of the sample transfer arm 24. The inner end 29 of the sample transfer arm is mounted to and extends radially outwardly from a cylindrical arm support member 30 which is received within three cylindrical sleeves 31, 32, and 33, as best shown in FIG. 2, which are telescoped over each other. The sleeves 31–33 are supported on a base member 36 within which is located a drive shaft 38 which is coupled to the arm support member 30 by a drive arrangement 39 for rotating the cylindrical member 30 to rotate the transfer arm 24 as best shown in FIGS. 2, 3 and 4. As will be explained in greater detail hereinafter, according to the teachings of the present invention, the drive arrangement 39 includes a lost motion clutch assembly 40.

As shown, the first sleeve 31 has a generally rectangularly shaped first window formed therein which is defined in part by one side edge 41 that forms a locating edge or stop and through which the arm 24 extends. Likewise the second sleeve 32 has a generally rectangularly shaped second window therein in registry with the first window and with one side edge 42 thereof forming a locating edge or stop. Similarly, the third or outer cylindrical sleeve 33 has a generally rectangularly shaped third window therein in registry with the other windows and with one side edge 43 thereof defining a locating edge or stop.

Also as best shown in FIGS. 2 and 3, the cylindrical sleeve 31 has a larger diameter, lower, cylindrical shell portion 46 integral therewith. The shell portion 46 is received over a stationary sleeve 48 and fixed thereto by means of a set screw 50 (FIG. 3). The second sleeve 32 is fixed to the first sleeve 31 by means of a set screw 52. The outer sleeve 33 is received over the second sleeve 32 and has two ball bearing detents 54 and 56 which are mounted on the inside top thereof and which are adapted to be received in one or the other of a pair of notches 58 and 60 formed on the top annular edge of the second sleeve 32. As shown in FIG. 2, the third sleeve 33 is fixed by a screw to the second sleeve 32.

Before describing the remaining parts of the sample transfer arm assembly 22, the arrangement and function of the three sleeves 31, 32 and 33 will now be described with particular reference to FIGS. 4, 5 and 6. In this respect, when the transfer sample arm assembly 22 is assembled for operation, the sample transfer arm extending through the aligned windows in the sleeves 31–33 is positioned with the outer end 27 thereof located above a sample cuvette 20 in the sample tray 14. This is best shown in FIG. 4. Then the inner or first sleeve 31 is rotated counterclockwise on the stationary cylinder 48 until the locating edge 41 bears against the sample transfer arm 24. Then the set screw 50 is tightened to lock the first sleeve 31 in that position where the side edge 41 provides and defines a locating stop for limiting clockwise arcuate movement of the arm 24 where the outer end thereof is located over a sample cuvette 20 as shown in FIG. 4.

The arcuate extent of the window in the first sleeve 31 from the one side edge 41 to a second side edge 71 is slightly greater than the arcuate travel required to rotate the sample transfer arm 24 from the first position over the sample cuvette 20 as shown in FIG. 4 to a second position where the sample transfer arm is located over the innermost well 14 as shown in FIG. 5. The proper positioning of the arm 24 over is accomplished by locating the transfer arm 24 with the outer end 27 thereof located over the innermost well 14 in the channel 13. Then the second sleeve 32 is rotated clockwise until the side edge 42 of the window therein engages the sample transfer arm 24. Next the set screw 52 is tightened to lock the second or intermediate sleeve 32 to the first or inner sleeve 31 with the edge 42 of the window forming a locating stop for the innermost position of the end 27 of the arm 24 over the innermost well 14 of a channel 13 in the transfer disc 12. In this position, the ball bearing detents 54 and 56 of the third sleeve 33 are located in the notches 58 so that the locating edge 43 of the window therein is radially aligned with the locating edge 42 of the window in the sleeve 32 on a line parallel to a radius extending outwardly from the axis 59 of rotation of the cylindrical arm support member 30 as shown in FIG. 5.

Once these positions are determined and the sleeves 31 and 32 locked in place, the notches 60 in the top edge of the second sleeve 32 automatically define a position for the sleeve 33 when the detents 54 and 56 are received in the notches 60 where the locating edge 43 of the window therein will locate the outer end 27 of the arm 24 over the second well 15 in one of the channels 13 when the arm 24 bears against the locating edge or stop 43 as best shown in FIG. 6.

In the operation of the sample transfer arm assembly 22 so far described, the drive shaft 38 will be rotated a predetermined arcuate extent by a prime mover (not shown) which will ideally move the arm 24 to a position against the locating edge 41 in the window of the sleeve 31. Then a reciprocating mechanism (not shown) will be operated to lower the shaft 38 thereby to lower the dip tube 28 into a sample cuvette 20. Next the shaft 38 is raised and rotated by the prime mover, ideally the predetermined arcuate extent, sufficient to bring the arm 24 into engagement with the side edges 42 and 43 of the windows in the second and third sleeves 32 and 33 to position the outer end 27 of the arm 24 over the innermost well 14. This is assuming, of course, that it is desired to place sample in the innermost well 14. Of course, if it is desired to place the sample in the second well 15, then the locating edge 43 would be positioned as shown in FIG. 6 and the prime mover would be set to rotate the arm support member 30 a shorter arcuate extent sufficient to bring the arm 24 into contact with the locating stop 43 of the sleeve 33.

It will be appreciated that control of the prime mover for rotating the shaft 38 to rotate such shaft 38 a very limited arcuate distance between the locating edges 41 and 42 is very difficult if at all possible. As a result, over-rotation of the shaft 38 is often encountered such that with the previously utilized drive arrangement, stress is placed on the arm 24 when it engages one of the locating stops 41 or 42 (or 43) with the result that a bending moment would be placed on the arm 24 and a twisting torque would be placed on the shaft 38 and the cylindrical support member 30.

In accordance with the teachings of the present invention, this problem is obviated by the provision of the drive arrangement 39 with the lost motion clutch assembly 40 which will now be described in detail with reference to FIGS. 2, 3, 7 and 8.

The drive arrangement 39 between the drive shaft 38 and the cylindrical support member 30 includes a flat generally rectangular cam member 80, which has rounded sides 81 and 82 and flat sides 83 and 84 and is fixed to a pin 85. In turn, the pin 85 is received within an axial bore 86 in the top end 87 of the drive shaft 38. A set screw 88 is provided for fixing the pin 85 within the bore 86 to properly locate the cam 80.

The drive arrangement 39 also includes a generally rectangular slot 90 which extends axially inwardly of the cylindrical support member 30 from the lower end thereof with the slot 90 being defined between opposed sidewalls 91 and 92 and an inner bottom wall 93 in the lower end of the cylindrical support member 30. The width of the slot 90 between sidewalls 91 and 92 is greater than the thickness of the cam 80 between the rounded sides 81 and 82 thereof thereby to permit rotation of the flat cam member 80 within the slot 90.

In accordance with the teachings of the present invention, the lost motion clutch assembly 40 is defined by a wide, generally U-shaped spring clip 100 and the interaction thereof with the cam 80 and slot 90. As shown, in clip 100 has a generally rectangular bight portion 102 which is sized and arranged to fit within the slot 90 against the inner wall 93 between the sidewalls 91 and 92 of the slot 90. The spring clip 100 further includes two leg portions 104 and 106 which extend angularly from the bight portion 102 and toward each other. Each leg portion 104 and 106 is flared at the outer end thereof to provide rounded bead formations 108, 110 and an outer edge 112, 114 which is located outwardly of the plane of the leg portion 104, 106. The space between the bead formations 110 and 112 is less than the thickness of the flat cam member 80 between the flat sides 83 and 84 thereof. As a result, when the cam member 80 is received within the slot 90 and between the leg portions 104 and 106 of the spring clip 100, the rounded bead formations 112 and 114 resiliently and frictionally bear against the flat sides 83 and 84 of the cam member.

The spring clip 100 is preferably made from, i.e., punched from, a flat piece of 0.020 thick phosphor bronze having a 510 spring tempered hardness.

In the operation of the lost motion clutch assembly 40, when the drive shaft 38 is rotated, the pin 85 is also rotated to rotate the cam 80 and this rotary motion is transmitted to the spring clip 100 as a result of the bearing engagement between the leg portions 104 and 106 and the cam 80. This motion transmitted to the spring clip 100 is transmitted by the bight portion 102, bearing against the sidewalls 91 and 92, to the cylindrical support member 30 to cause rotation of the support member 30.

However, and as best shown in FIGS. 7, 8, and 9 when the drive shaft 38 is rotated a greater arcuate extent than the arcuate extent between the locating stops 41 and 42 or 43, i.e., to the position shown in FIG. 5 or 6, movement of the cylindrical arm support member 30 is prevented as a result of engagement of arm 24 with the locating stop 42 or 43. In this situation, the cam member 80 is allowed to turn against the spring action of the leg portions 104 and 106 of the spring clip 100, to spread them apart and move them outwardly with the slot 90 as shown in FIG. 8. To facilitate this movement, the cam member 80 has the rounded edges 81 and 82.

With the lost motion movement described above, undesired stresses which could be brought about by the bearing engagement of the sample transfer arm 24 against a locating stop 42 (or 43 or 41) is prevented. Also, it will be appreciated that when the drive shaft 38 is rotated to rotate in the opposite direction, the cam 80 will first move from the position shown in FIG. 8 to the position shown in FIG. 7 and then rotate the arm 24 until the transfer arm 24 engages the locating stop 41.

It will be noted that the lost motion clutch assembly 40 allows lost motion movement between the cam 80 and the cylindrical arm support member 30 without damage to the sample transfer arm assembly 22 when the arcuate extent of movement of the drive shaft 38 is not set in precise registry with the positions of the locating stops 41 and 42 or 43. In this way, allowance for error in the settings of the movement of the drive shaft 38 are compensated for with the lost motion clutch assembly 40.

From the foregoing description it will be apparent that the lost motion clutch assembly 40 of the present invention has a number of advantages, particularly the advantage described above of preventing damage to the sample transfer arm assembly 22 while allowing for accurate positioning of the sample transfer arm 24 at and between two or three positions, and other advantages which are inherent in the invention. Also it will be apparent from the foregoing description that obvious modifications and variations can be made to the lost motion clutch assembly 40 of the present invention without departing from the teachings of the invention. Accordingly, the scope of the invention is only to be limited as necessitated by the accompanying claims.

We claim:

1. An improved sample transfer arm assembly for use in a device for transferring liquid sample from a first receptacle to a second receptacle, said assembly including a sample transfer arm, support means for supporting said transfer arm with said arm extending normal to and from the axis of said support means, locating means for locating and limiting arcuate movement of said arm about said axis of said support means, drive means including a drive shaft for rotating said arm support means a predetermined arcuate extent between a first position where the outer end of said arm is located over the first receptacle and at least one other position where said outer end of said transfer arm is located over the second receptacle, and said drive means including lost motion clutch means between said drive shaft and said arm support means for permitting overrotation of said drive shaft beyond predetermined arcuate extent without damage to said sample transfer arm when arcuate movement of said sample transfer arm is limited by engagement thereof with said locating means.

2. The assembly according to claim 1 wherein said support means comprises a generally cylindrical member having a radial opening therein for receiving the inner end of said sample transfer arm and having a wide slot formed in one end thereof, said slot extending inwardly of said one end along and on either side of the axis of said cylindrical member and having a generally rectangular cross-section, and wherein said drive means includes a flat cam member which is fixed to the outer end of said drive shaft, which has a generally rectangular cross-section and which is received in said slot.

3. The assembly according to claim 2 wherein the width of said cam member is less than the width of said slot and wherein said lost motion clutch means comprises a wide, generally U-shaped spring clip having a bight portion sized to fit within and at the inner end of said slot and having two leg portions which extend toward each other, the outer ends of said leg portions being spaced apart less than the width of said cam member, and said spring clip being received in said slot with said ends of said leg portions frictionally and resiliently engaging opposite sides of said flat cam member.

4. The assembly according to claim 3 wherein said corner edges of said cam member are rounded to facilitate sliding engagement thereof with said flat leg portions when said cam rotates within said slot against said leg portions and rotational movement of said cylindrical arm support member is stopped by engagement of said sample transfer arm with said locating means.

5. The assembly according to claim 3 wherein the outer ends of each of said flat leg portions is flared outwardly to provide an inwardly facing bead formation facing toward and engaging one side of said flat cam member and an outer edge located outwardly of the plane of said flat leg portion.

6. The assembly according to claim 3 wherein said bight portion is a flat generally rectangularly shaped bight portion which is sized to fit within said slot at the inner end thereof so as to engage the sidewalls of said slot.

7. The assembly according to claim 3 wherein said spring clip is formed by deforming a rectangular flat strip of spring metal into a U shape.

8. The assembly according to claim 7 wherein said spring clip is made of a phosphor bronze material having a 510 spring tempered hardness.

9. The assembly according to claim 7 wherein said spring clip is made from a rectangular flat strip of spring metal having a thickness of approximately 0.020 inches.

* * * * *